United States Patent
Yuan

(10) Patent No.: US 6,211,187 B1
(45) Date of Patent: *Apr. 3, 2001

(54) 3-ARYL SUBSTITUTED PYRAZOLO[4,3-D] PYRIMIDINE DERIVIATIVES; CORTICOTROPIN-RELEASING FACTOR RECEPTOR ($CRF_1$) SPECIFIC LIGANDS

(75) Inventor: Jun Yuan, Guilford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/341,024

(22) PCT Filed: Dec. 23, 1997

(86) PCT No.: PCT/US97/24172

§ 371 Date: Oct. 22, 1999

§ 102(e) Date: Oct. 22, 1999

(87) PCT Pub. No.: WO98/29413

PCT Pub. Date: Jul. 9, 1998

Related U.S. Application Data

(63) Continuation of application No. 08/775,404, filed on Dec. 31, 1996, now Pat. No. 5,723,608.

(51) Int. Cl.[7] ...................... C07D 487/04; A61K 31/519
(52) U.S. Cl. ................. 514/258; 544/283; 544/61; 544/262; 540/467; 540/470; 540/481
(58) Field of Search ............. 544/283, 61, 262; 540/467, 470, 481; 514/258

(56) References Cited

U.S. PATENT DOCUMENTS

| | | | |
|---|---|---|---|
| 4,605,642 | 8/1986 | Rivier et al. | 514/12 |
| 5,063,245 | 11/1991 | Abreu et al. | 514/404 |
| 5,644,057 | 7/1997 | Yuan et al. | 544/280 |
| 5,723,608 | * 3/1998 | Yuan | 544/283 |

FOREIGN PATENT DOCUMENTS

| | | |
|---|---|---|
| 210 265 | 6/1984 | (DE). |
| 0 691 128 A1 | 1/1996 | (EP). |
| 1103061 | 1/1993 | (GB). |
| WO 96/01254 | 1/1986 | (WO). |
| WO 94/13643 | 6/1994 | (WO). |
| WO 94/13644 | 6/1994 | (WO). |
| WO 94/13661 | 6/1994 | (WO). |
| WO 94/13676 | 6/1994 | (WO). |
| WO 94/13677 | 6/1994 | (WO). |
| WO 95/33750 | 12/1995 | (WO). |
| WO 96/35689 | 11/1996 | (WO). |
| WO 97/29109 | 8/1997 | (WO). |

OTHER PUBLICATIONS

Takei, et al., (1979), "A New Synthetic Method for Some Pyrazolo [4,3–d]pyrimidines," Bull. Chem. Soc. Of Japan., vol. 52, No. 1, pp. 208–211.

Grigoriadis et al., (1991), "Biochemical, Pharmacological, and Autoradiographic Methods to Study Corticotropin–Releasing Factor Receptors," Methods in Neurosciences, vol. 5, pp. 510–538.

Owens et al., (1991), "Physiology and Pharmacology of Corticotropin–releasing Factor," Pharm Rev., vol. 43, No. 4, pp. 425–473.

Montgomery et al., (1972), "The Use of Enamines in the Synthesis of Heterocycles," J. Het. Chem., vol. 9, pp. 1077–1079.

Sindler–Kulyk, M., et al., (1983), "Photocycloaddition Reactions of 3–Phenyl–1, 2–benzisothiazole and Alkynes," J. Org. Chem., vol. 48, pp. 1275–1281.

Holava, Jr., et al., (1969), "1–Substituted 4–Aryl (or 4–Aralkyl–) phthalazines, " New Compounds, vol. 12, pp. 555–556.

Avila et al., (1987), "Biological Action of Pyrazolopyrimidine Derivatives Against Trypanosoma Cruzi. Studies in Vitro and in Vivo", Comp. Biochem. Physiol. vol. 86C, No. 1, pp. 49–54.

* cited by examiner

Primary Examiner—Mukund J. Shah
Assistant Examiner—Hong Liu
(74) Attorney, Agent, or Firm—Steve J. Sarussi; McDonnell Boehnen Hulbert & Berghoff

(57) ABSTRACT

This invention encompasses compounds of the formula

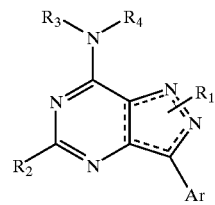

wherein
Ar represents a mono- , di- or trisubstituted aryl group where at least one position on Ar ortho to the point of attachment to the pyrazole ring is substituted; and
$R_1$ represents lower alkyl;
$R_2$ is hydrogen or lower alkyl; and
$R_3$ and $R_4$ independently represent organic and inorganic substituents,
which compounds are highly selective partial agonists or antagonists or human $CRF_1$ receptors and are useful in the diagnosis and treatment of treating stress related disorders such as post traumatic stress disorder (PTSD) as well as depression, headache and anxiety.

14 Claims, No Drawings

3-ARYL SUBSTITUTED PYRAZOLO[4,3-D] PYRIMIDINE DERIVIATIVES; CORTICOTROPIN-RELEASING FACTOR RECEPTOR (CRF₁) SPECIFIC LIGANDS

This application is a national phase application filed under 35 U.S.C. § 371 of International Application No. PCT/US97/24172 filed Dec. 23, 1997, which is a continuation of and claims benefit of U.S. application Ser. No. 08/775,404 filed Dec. 31, 1996, now U.S. Pat. No. 5,723,608.

BACKGROUND OF THE INVENTION

1. Field of the Invention

This invention relates to certain pyrazolo[4,3-d] pyrimidine derivatives which selectively bind to corticotropin-releasing factor (CRF) receptors. More specifically, the invention relates to 3-aryl substituted pyrazolo[4,3-d]pyrimidine derivatives. The invention further relates to pharmaceutical compositions comprising such compounds. It also relates to the use of such compounds in treating stress related disorders such as post traumatic stress disorder (PTSD) as well as depression, headache and anxiety.

2. Description of the Related Art

International Application PCT/US93/11333 describes pyrazolo[3,4-d]pyrimidines said to be CRF antagonists. Bull. Chem. Soc. Japan. 52(1), 208–11, (1979) describes the synthesis of 3-phenyl-pyrazolo[4,3-d]pyrimidines.

SUMMARY OF THE INVENTION

This invention provides novel compounds of Formula I which interact with CRF receptors.

The invention provides pharmaceutical compositions comprising compounds of Formula I. It further relates to the use of such compounds in treating stress related disorders such as post traumatic stress disorder (PTSD) as well as depression, headache and anxiety. Accordingly, a broad embodiment of the invention is directed to a compound of Formula I:

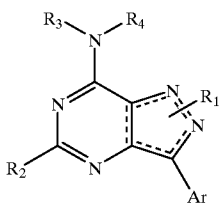

I wherein
Ar is phenyl, 1- or 2- naphthyl, 2-, 3-, or 4-pyridinyl, 2- or 3- thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the pyrazole ring is substituted;
$R_1$ is lower alkyl;
$R_2$ is hydrogen, halogen, lower alkyl, lower alkoxy, or thioalkoxy having 1–6 carbon atoms;
$R_3$ and $R_4$ are the same or different and represent hydrogen, lower alkyl, alkoxy lower alkyl, hydroxy lower alkyl, or alkenyl;
phenyl, 2-, 3-, or 4- pyridinyl, 2- or 3-thienyl or 2-, 4- or 5-pyrimidinyl, each of which is optionally mono- or disubstituted with halogen, hydroxy, lower alkyl, or lower alkoxy;
phenyl-, 2-, 3-, or 4-pyridinyl-, 2- or ³-thienyl-, or 2-, 4- or ⁵-pyrimidinyl-lower alkyl, each of which is optionally mono- or disubstituted with lower alkyl;
cycloalkyl or cycloalkyl lower alkyl, each of which is optionally mono- or disubstituted with lower alkyl; or
2-hydroxyethyl or 3-hydroxypropyl, each of which is optionally monosubstituted with lower alkyl;
provided that not both $R_3$ and $R_4$ are hydrogen; or
$R_3$ and $R_4$ taken together represent —$(CH_2)_n$—A—$(CH_2)_m$— where n is 2,or3;
A is methylene, 1,2-phenylene, oxygen sulfur or $NR_6$, wherein $R_6$ is lower alkyl, phenyl, 2-, 3-, or 4-pyridinyl, 2-or 3-thienyl or 2-, 4- or 5-pyrimidinyl, or phenyl-, 2-, 3-or 4-pyridinyl-, 2-or 3-thienyl-, or 2-, 4- or 5-pyrimidinylalkyl; and
m is 1,2 or 3.

These compounds are highly selective partial agonists or antagonists at CRF receptors and are useful in the diagnosis and treatment of stress related disorders such as post traumatic stress disorder (PTSD) as well as depression and anxiety.

DETAILED DESCRIPTION OF THE INVENTION

In addition to the compounds of Formula I above, the invention encompasses of Formula II:

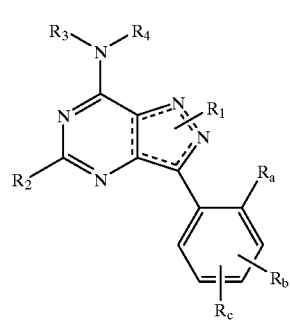

II wherein
$R_a$ represents halogen, hydroxy, lower alkyl, or lower alkoxy;
$R_b$, and $R_c$ independently represent hydrogen, halogen, hydroxy, lower alkyl, or lower alkoxy;
$R_1$ is lower alkyl;
$R_2$ is hydrogen or lower alkyl; and
$R_3$ and $R_4$ are the same or different and represent hydrogen, lower alkyl, lower alkenyl, cycloalkyl, cycloalkyl lower alkyl, 2-hydroxyethyl or 3-hydroxypropyl;
provided that not both $R_3$ and $R_4$ are hydrogen.

Preferred compounds of Formula II are those where $R_3$ and $R_4$ independently represent $C_1$–$C_6$ alkyl (i.e., lower alkyl) optionally substituted with halogen, hydroxy, or $C_1$–$C_6$ alkoxy, Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the pyrazole ring is substituted. More preferred compounds of Formula II are those where Ar is phenyl that is trisubstituted with $C_1$–$C_6$ alkyl, with the proviso that at least one of the positions on the phenyl group ortho to the point of attachment to the pyrazole ring is substituted. Most preferred compounds of Formula II are those where Ar is phenyl that is trisubstituted in the 2, 4, and 6 positions (para and both ortho positions relative to the point of attachment to the pyrazole ring) with $C_1-C_3$ alkyl, most preferably methyl. Particularly preferred compounds of Formula II are those where $R_3$ and $R_4$ are independently hydrogen or $C_1-C_4$ alkyl, e.g., methyl, ethyl, propyl, butyl, or cyclopropylmethyl, provided not both $R_3$ and $R_4$ are hydrogen.

The invention further encompasses compounds of Formula III:

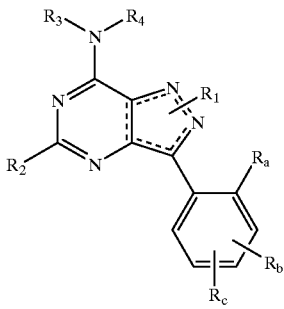

III wherein
$R_a$ represents halogen, hydroxy, lower alkyl, or lower alkoxy;
$R_b$, and $R_c$ independently represent hydrogen, halogen, hydroxy, lower alkyl, or lower alkoxy;
$R_1$ is lower alkyl;
$R_2$ is hydrogen or lower alkyl; and
$R_3$ and $R_4$ are the same or different and represent hydrogen, lower alkyl, cycloalkyl, cycloalkyl lower alkyl, or alkenyl;
  phenyl, 2-, 3-, or 4- pyridinyl, or 2-, 4- or 5-pyrimidinyl, each of which is optionally mono- or disubstituted with halogen, hydroxy, lower alkyl, or lower alkoxy; or
  phenyl-, 2-, 3-, or 4pyridinyl-, or 2-, 4- or 5-pyrimidinyl- lower alkyl, each of which is optionally mono- or disubstituted with lower alkyl,
provided that not both $R_3$ and $R_4$ are hydrogen.

Further, the invention encompasses compounds of Formula IV:

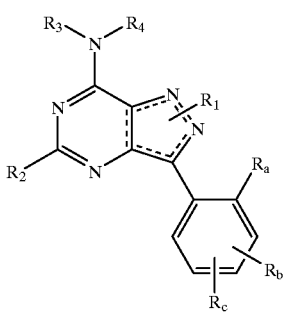

IV wherein
$R_a$ represents halogen, hydroxy, lower alkyl, or lower alkoxy;
$R_b$, and $R_c$ independently represent hydrogen halogen, hydroxy, lower alkyl, or lower alkoxy;
$R_1$ is lower alkyl;
$R_2$ is hydrogen or lower alkyl; and
$R_3$ and $R_4$ taken together represent with the nitrogen atom to which they are attached represent $-(CH_2)_n-A-(CH_2)_m-$ where n is 2, or 3;
A is methylene, 1,2-phenylene, oxygen, sulfur or $NR_6$, wherein $R_6$ is lower alkyl, phenyl, 2-, 3-, or 4-pyridinyl, 2-or 3-thienyl or 2-, 4- or 5-pyrimidinyl, or phenyl-, 2-, 3-or 4-pyridinyl-, 2-or 3-thienyl-, or 2-, 4- or 5-pyrimidinylalkyl; and
m is 1,2 or 3.

Preferred compounds of the invention have Formula V:

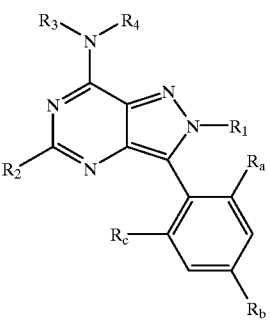

V wherein
$R_a$, and $R_b$ and $R_c$ independently represent hydrogen, halogen, hydroxy, lower alkyl, or lower alkoxy, with the proviso that not both $R_a$ and $R_c$ are hydrogen;
$R_1$ is lower alkyl;
$R_2$ is hydrogen or lower alkyl; and
$R_3$ and $R_4$ are the same or different and represent hydrogen, lower alkyl, cycloalkyl, cycloalkyl lower alkyl, alkenyl, 2-hydroxyethyl or 3-hydroxypropyl, provided that not both $R_3$ and $R_4$ are hydrogen.

Other preferred compounds of Formula V are those where $R_3$ and $R_4$ independently represent $C_1-C_6$ alkyl (i.e., lower alkyl) optionally substituted with halogen, hydroxy, or $C_1-C_6$ alkoxy.

More preferred compounds of Formula V are those where $R_a$, $R_b$, and $R_c$ are methyl. Particularly preferred compounds of Formula V are those where $R_a$, $R_b$, and $R_c$ are methyl, $R_1$ and $R_2$ independently represent lower alkyl, and $R_3$ and $R_4$ are independently hydrogen or $C_1-C_4$ alkyl, e.g., methyl, ethyl, propyl, butyl, or cyclopropylmethyl, provided not both $R_3$ and $R_4$ are hydrogen.

Other preferred compounds of the invention have Formula VI:

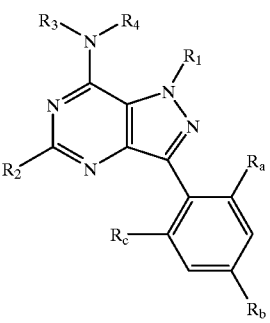

VI wherein
$R_a$, $R_b$, and $R_c$ independently represent hydrogen, halogen, hydroxy, lower alkyl, or lower alkoxy, with the proviso that not both $R_a$ and $R_c$ are hydrogen;
$R_1$ is lower alkyl;

$R_2$ is hydrogen or lower alkyl; and
$R_3$ and $R_4$ are the same or different and represent hydrogen, lower alkyl, cycloalkyl, cycloalkyl lower alkyl, alkenyl, 2-hydroxyethyl or 3-hydroxypropyl, provided that not both $R_3$ and $R_4$ are hydrogen.

Other preferred compounds of Formula VI are those where $R_3$ and $R_4$ independently represent $C_1$–$C_6$ alkyl (i.e., lower alkyl) optionally substituted with halogen, hydroxy, or $C_1$–$C_6$ alkoxy.

More preferred compounds of Formula VI are those where $R_a$, $R_b$, and $R_c$ are methyl. Particularly preferred compounds of Formula VI are those where $R_a$, $R_b$, and $R_c$ are methyl, $R_1$ and $R_2$ independently represent lower alkyl, and $R_3$ and $R_4$ are independently hydrogen or $C_1$–$C_4$ alkyl, e.g., methyl, ethyl, propyl, butyl, or cyclopropylmethyl, provided not both $R_3$ and $R_4$ are hydrogen.

The invention also encompasses intermediates for preparing compounds of Formula I. Among these intermediates are compounds of Formula VII:

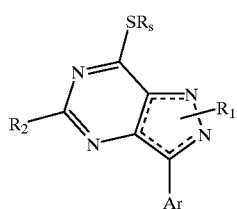

VII wherein
$R_s$ is hydrogen or lower alkyl;
$R_1$ and $R_2$ are as defined above for Formula I;
$R_a$ is hydrogen or $R_bO_2C$— where $R_b$ represents $C_1$–$C_6$ alkyl; and
Ar is phenyl, 1- or 2- naphthyl, 2-, 3-, or 4-pyridinyl, 2- or 3- thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the pyrazole ring is substituted.

Preferred Ar groups are 2,4,6-tri($C_1$–$C_6$)alkylphenyl groups, most preferably 2,4,6-trimethylphenyl groups. Preferred $R_s$ groups are hydrogen and methyl.

The invention further encompasses intermediates of Formula VIII:

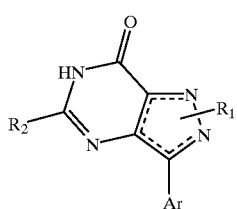

VIII wherein
$R_1$ and $R_2$ are as defined above for Formula I;
$R_a$ is hydrogen or $R_bO_2C$— where $R_b$ represents $C_1$–$C_6$ alkyl; and
Ar is phenyl, 1- or 2- naphthyl, 2-, 3-, or 4-pyridinyl, 2- or 3- thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the pyrazole ring is substituted.

Preferred Ar groups are 2,4,6-tri($C_1$–$C_6$)alkylphenyl groups, most preferably 2,4,6-trimethylphenyl groups.

The invention further encompasses intermediates of Formula IX:

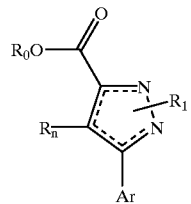

IX wherein
$R_o$ is hydrogen or lower alkyl;
$R_1$ and $R_2$ are as defined above for Formula I; and
Ar is phenyl, 1- or 2- naphthyl, 2-, 3-, or 4-pyridinyl, 2- or 3- thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the pyrazole ring is substituted.

Preferred Ar groups are 2,4,6-tri($C_1$–$C_6$)alkylphenyl groups, most preferably 2,4,6-trinmethylphenyl groups. Preferred $R_o$ groups are methyl and ethyl.

Also, intermediates of Formula X are within the invention:

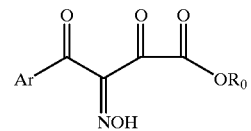

X wherein
$R_o$ is hydrogen or lower alkyl;
$R_1$ and $R_2$ are as defined above for Formula I; and
Ar is phenyl, 1- or 2- naphthyl, 2-, 3-, or 4-pyridinyl, 2- or 3- thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the alkyl 2,4-dioxo-3-oximinobutanoate moiety is substituted.

Preferred Ar groups are 2,4,6-tri($C_1$–$C_6$)alkylphenyl groups, most preferably 2,4,6-trimethylphenyl groups. Preferred $R_o$ groups are methyl and ethyl.

The invention also encompasses compounds of Formula XI:

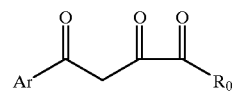

XI where
$R_o$ is hydrogen or lower alkyl;
$R_1$ and $R_2$ are as defined above for Formula I; and
Ar is phenyl, 1- or 2- naphthyl, 2-, 3-, or 4-pyridinyl, 2- or 3- thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the alkyl-2,4-dioxobutanoate moiety is substituted.

Preferred Ar groups are 2,4,6-tri($C_1$–$C_6$)alkylphenyl groups, most preferably 2,4,6-trimethylphenyl groups. Preferred $R_o$ groups are methyl and ethyl.

Representative compounds of the present invention, which are encompassed by, Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

When a compound of formula I is obtained as a mixture of enantiomers these may be separated by conventional methods such as crystallization in the presence of a resolving agent, or chromatography, for example, using a chiral HPLC column.

In the compounds of the invention the Ar group is preferably a phenyl group that is; mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the isoquinolinanine or phthalazinamine ring is substituted. Where Ar is phenyl, the carbon atom by which the phenyl group is attached to the pyrazole ring is defined as the 1-position. Thus, the positions ortho to the point of attachment are the 2 and 6 positions, and the para position is the 4-position of the phenyl group.

By the terms ($C_1$–$C_6$)alkyl and lower alkyl is meant straight and branched chain alkyl groups having from 1–6 carbon atoms as well as cyclic alkyl groups such as, for example, cyclopropyl, cyclobutyl, or cyclohexyl. Specific examples of such alkyl groups are methyl, ethyl, propyl, isopropyl, n-butyl, isobutyl, tert-butyl, sec-butyl, neopentyl and n-pentyl. Preferred $C_1$–$C_6$ alkyl groups are methyl, ethyl, propyl, butyl or cyclopropylmethyl.

By the terms ($C_1$–$C_6$)alkoxy and lower alkoxy is meant straight and branched chain alkoxy groups having from 1–6 carbon atoms.

By hydroxy $C_1$–$C_6$ alkyl or hydroxyalkyl is meant a $C_1$–$C_6$ alkyl group carrying a terminal hydroxy moiety.

By $C_1$–$C_6$ alkoxy $C_1$–$C_6$ alkyl (alkoxy lower alkyl) is meant a group of the formula —$(CH_2)_xO(CH_2)_yCH_3$, where x and y independently represent integers of from 1–6.

By the term $C_1$–$C_6$ alkenyl or lower alkenyl is meant straight or branched chain hydrocarbon groups having from 1–6 carbon atoms and at least one double bond.

By halogen, halo, or halide is meant fluorine, chlorine, bromine and iodine substituents.

By aryl($C_1$–$C_6$)alkyl, e.g., phenylalkyl, pyridinylalkyl, pyrimidinylalkyl, and thienylalkyl, is meant aryl groups attached to the parent group by a straight or branched chain alkyl group having 1–6 carbon atoms. Thus, the aryl groups include phenyl, 1- or 2-naphthyl, 2-, 3-, or 4-pyridinyl, 2- or 3-thienyl or 2-, 4-, or 5- pyrimidinyl. These aryl groups are optionally substituted with up to two groups selected from halogen, hydroxy, ($C_1$–$C_6$ )alkyl, and ($C_1$–$C_6$)alkoxy.

Representative examples of compounds according to the invention are shown in Table 1 below.

TABLE 1[1]

| Compound No. |
| --- |
| 1 |
| 2 |
| 3 |

The pharmaceutical utility of compounds of this invention is indicated by the following assay for CRF receptor activity.

Assay for CRF receptor binding activity

CRF receptor binding is performed using a modified version of the assay described by Grigoriadis and De Souza (Biochemical, Pharmacological, and Autoradiographic Methods to Study Corticotropin-Releasing Factor Receptors. Methods in Neurosciences, Vol. 5, 1991). Membrane pellets containing CRF receptors are resuspended in 50 mM Tris buffer pH 7.7 containing 10 mM $MgCl_2$ and 2 mM EGTA and centrifuged for 10 minutes at 48000 g. Membranes are washed again and brought to a final concentration of 1500 µg/ml in binding buffer (Tris buffer described above with 0.1% BSA, 0.15 mM bacitracin and 0.01 mg/ml aprotinin.). For the binding assay, 100 µl of the membrane preparation is added to 96-well microtube plates containing 100 µl of $^{125}$I-CRF (SA 2200 Ci/mmol, final concentration of 100 pM) and 50 µl of drug. Binding is carried out at room temperature for 2 hours. Plates are then harvested on a Brandel 96 well cell harvester and filters are counted for gamma emissions on a Wallac 1205 Betaplate liquid scintillation counter. Non specific binding is defined by 1 uM cold CRF. $IC_{50}$ values are calculated with the non-linear curve fitting program RS/1 (BBN Software Products Corp., Cambridge, Mass.). The compounds of the invention typically have binding affinities, expressed as $IC_{50}$ values, of from about 0.5 nanomolar (nM) to about 10 micromolar (µM). The binding characteristics for representative examples of the invention are shown in Table 1.

TABLE I

| Compound Number | IC$_{50}$ (nM) |
|---|---|
| 1 | 1.4 |
| 3 | 1.8 |

Compound numbers relate to compounds described in the examples below:

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrastemal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents for example sodium carboxymethylcellulose, methylcellulose, hydropropylmethylcellulose, sodium alginate, polyvinylpyrrolidone, gum tragacanth and gum acacia; dispesing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifiing agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion drug combination and the severity of the particular disease undergoing therapy.

A representative illustration of methods suitable for the preparation of compounds of the present invention is shown in Scheme I. Those having skill in the art will recognize that the starting materials may be varied and additional steps employed to produce compounds encompassed by the present invention. For example, in certain situations, protection of reactive moieties such as amino groups will be required.

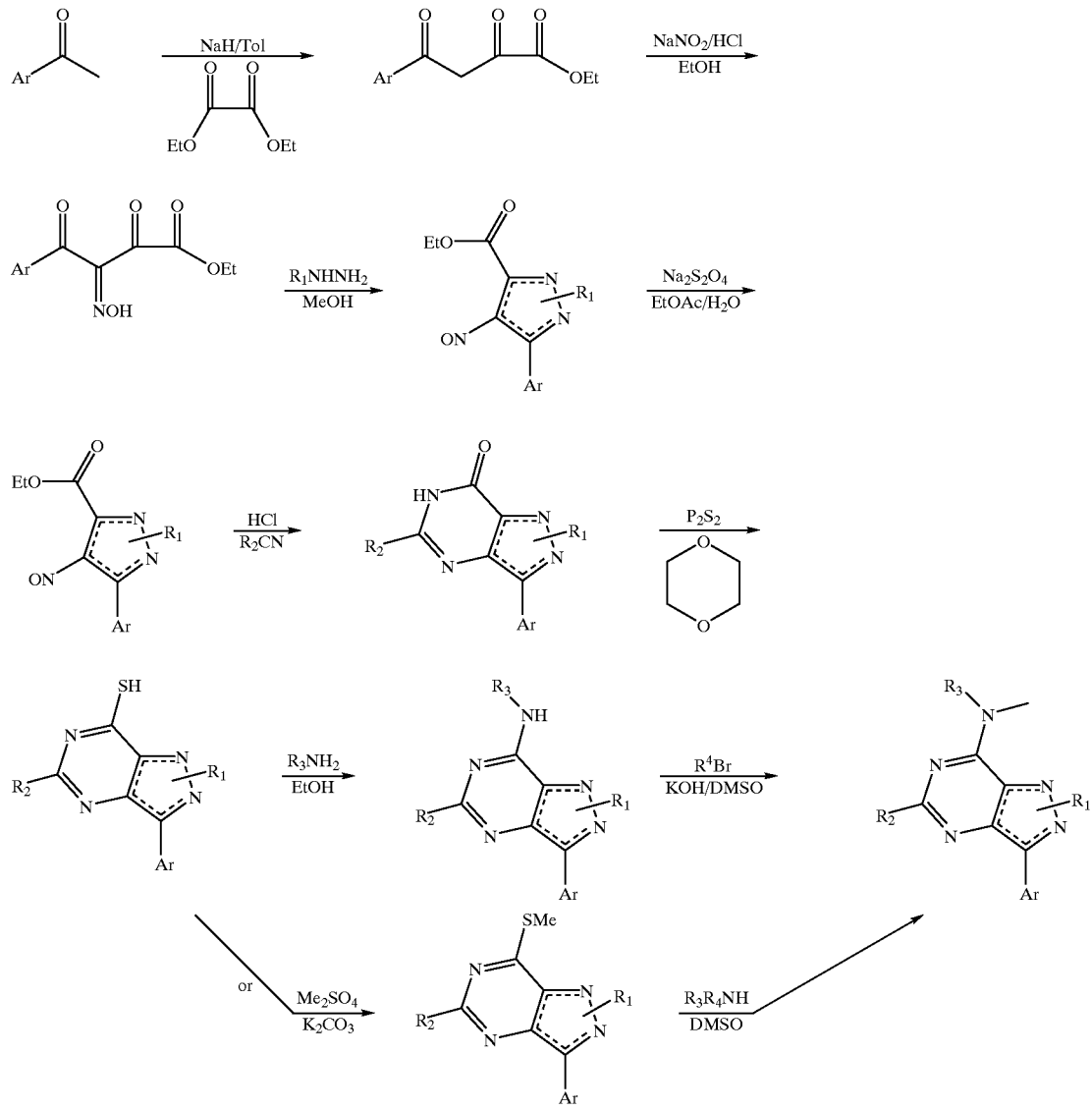

Scheme I

In the above scheme, $R_1$–$R_4$, and Ar carry the definitions set forth above for Formula I.

The disclosures in this application of all articles and references, including patents, are incorporated herein by reference.

The invention is illustrated further by the following examples which are not to be construed as limiting the invention in scope or spirit to the specific procedures and compounds described in them.

EXAMPLE 1

A. Ethyl 2,4-dioxo-4-(2,4,6-trimethylphenyl)butanoate

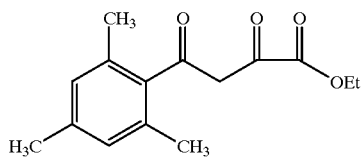

To a solution of 2',4',6'-trimethylacetophenone (15 g, 92.6 mmol) and diethyl oxalate (20 g, 139 mmol) in 500 mL of anhydrous toluene was cautiously added 7.4 g of NaH (60% dispersion in mineral oil). The reaction mixture was slowly heated to reflux under $N_2$. It was refluxed for about 20 minutes, then cooled, poured into ice-cold aqueous HCl solution, and extracted with ether. The extracts were washed with brine, dried over $Na_2SO_4$, filtered through a short silica gel pad and concentrated to give 16.2 g of a red oil which was used in the next reaction without further purification.

B. Ethyl 2,4-dioxo-3-oximino-4-(2,4,6-trimethylphenyl)butanoate

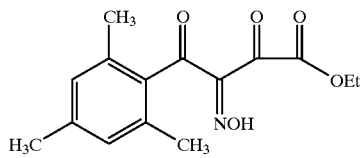

$N_2O_3$ gas was slowly passed into a stirred solution of the product of step A (16.2 g) in 300 mL of ethanol until the disappearance of starting material was confirmed by TLC. $N_2O_3$ gas was generated by the dropwise addition of 12N aqueous HCl solution into an aqueous slurry of $NaNO_2$. The solvent was removed from the mixture and 200 mL of water was added to the residue. The product was then extracted into ether. The ether extract was dried over $Na_2SO_4$ and evaporated to give 16.1 g of a semi-solid.

C. Ethyl 4-amino-1-methyl-5-(2,4,6-trimethylphenyl)pyrazole-3-carboxylate

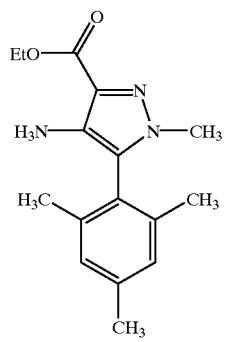

To a solution of the product of step B (4.0 g, 13.8 mmol) and 1.6 mL of 12N hydrochloric acid in 100 mL of methanol was added dropwise 0.63 g of methyl hydrazine at 0° C. The reaction mixture was stirred at room temperature 4 hours, and then concentrated. The resulting residue was partitioned between water and ethyl acetate. The organic phase was separated and washed once with brine. The ethyl acetate solution was then mixed with 100 mL of water. Solid $Na_2S_2O_4$ in excess was added in small portion until TLC showed completion of the reduction. The organic phase was separated, washed with water and brine, and dried over $Na_2SO_4$. Evaporation gave 3.1 g of the title compound as a foam.

D. 2,5-Dimethyl-3-(2,4,6-trimethylphenyl)-2,6-dihydro-2H-pyrazolo[4,3-d]pyrimidin-7-one

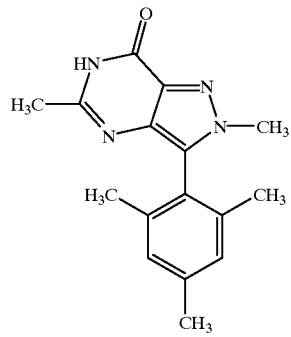

A solution of the product of step C (3.1 g) in 100 mL of anhydrous $CH_3CN$ was saturated with HCl gas, stirred at room temperature overnight, and then concentrated. The residue was partitioned between aqueous $NaHCO_3$ solution and ethyl acetate. The organic layer was separated, washed with brine dried over $Na_2SO_4$ and concentrated. The residue was triturated with ether. The solid was collected by filtration to give 1.0 g of the title compound as a white solid, m.p. 264–66° C.

E. 2,5-Dimethyl-3-(2,4,6-trimethylphenyl)-2,4-dihydro-2H-pyrazolo[4,3-d]pyrimidin-7-thione

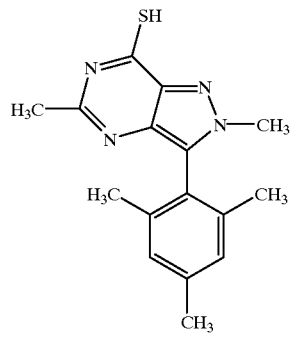

A mixture of the product of step D (0.6 g, 2.2 mmol) and $P_2S_5$ (1.0 g, 2.2 mmol) in 50 mL of dioxane was heated to reflux for 2 hours. The solvent was evaporated. The residue was partitioned between water and ethyl acetate. The organic layer was separated, washed with brine, dried over $Na_2SO_4$ and concentrated to give 0.60 g of the title compound as a yellow foam.

F. N-Propyl-2,5-dimethyl-3-(2,4,6-trimethylphenyl)-2H-pyrazolo[4,3-d]pyrimidin-7-amine

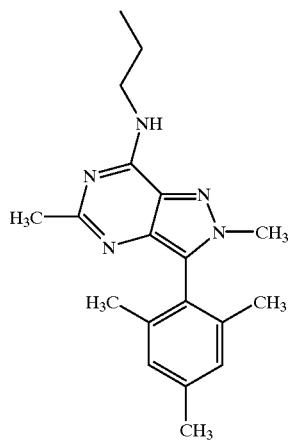

A solution of the product of step E (0.6 g) and 1 mL of propylamine in 10 mL of ethanol was heated to reflux for 3 hours. Evaporation of the volatile gave 550 mg of the title compound as a foam.

G. N,N-Dipropyl-2,5-dimethyl-3-(2,4,6-trimethylphenyl)-2H-pyrazolo[4,3-d]pyrimidin-7-amine (Compound 1)

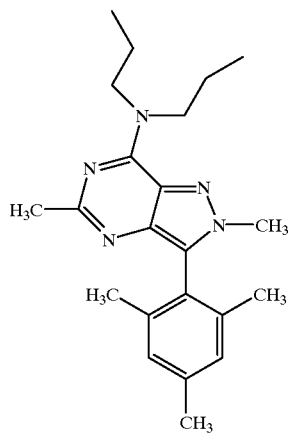

A mixture of the product of step F (400 mg, 1.2 mmol), powder KOH (1.0 g) and 1-bromopropane (1 mL) in 2 mL of DMSO was heated at 60° C. for 8 hours. The excess bromopropane was then evaporated. The mixture was partitioned between water and ether. The aqueous layer was separated and extracted with ether. The combined ether extracts were washed with water and brine, dried over $Na_2SO_4$ and concentrated to an oil. The oil was purified through silica gel column chromatography to give 260 mg of the title compound as an oil. $^1$H NMR (CDCl$_3$): d 0.97 (t, 6 H), 1.76 (m, 4 H), 1.96 (s, 6 H), 2.32 (s, 3 H), 2.45 (s, 3 H), 3.77 (s, 3 H), 3.40–4.30 (br, 4 H), 6.95 (s, 2 H) ppm. The hydrochloride salt prepared in Ether/HCl melted at 210–13° C.

EXAMPLE 2 and EXAMPLE 3

A. N-Ethyl-5-methyl-3-(2,4,6-trimethylphenyl)-1H-pyrazolo[4,3-d]pyrimidin-7-amine

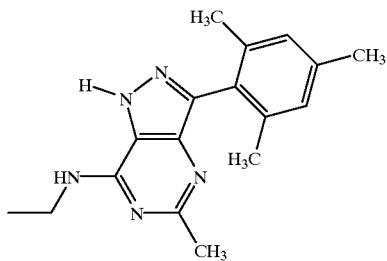

A solution of 5-Methyl-3-(2,4,6-trimethylphenyl)-1H-pyrazolo[4,3-d]pyrimidin-7-thione (250 mg, prepared in a manner similar to the compound of step E in Example 1) and 25 mL of ethylamine (2M in methanol) was heated to reflux for 3 hours. Evaporation of the volatile gave 255 mg of the title compound as a foam.

B. 1. N,N-Diethyl-1-ethyl-5-methyl-3-(2,4,6-trimethylphenyl)-1H-pyrazolo[4,3-d]pyrimidin-7-amine (Example 2) (Compound 2)

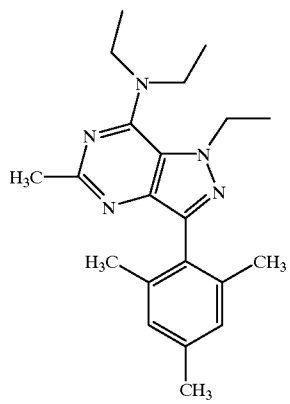

2. N,N-Diethyl-2-ethyl-5-methyl-3-(2,4,6-trimethylphenyl)-2H-pyrazolo[4,3-d]pyrimidin-7-amine (Example 3)

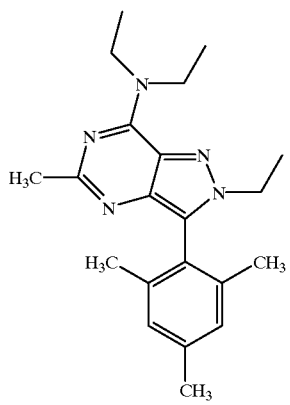

A mixture of the product of step A (250 mg, 0.85 mmol), powdered KOH (0.5 mg) and 1-bromopropane (0.5 mL) in 2 mL of DMSO was heated at 60° C. for 2 hours. The excess bromopropane was then evaporated. The mixture was partitioned between water and ether. The aqueous layer was separated and extracted with ether. The combined ether extracts were washed with water and brine, dried over $Na_2SO_4$ and concentrated to an oil. The oil was purified through silica gel column chromatography using Hexane/ EtOAc (100/30, v/v). The faster moving fraction, comprising the titled compound (example 2 ) was collected. Evaporation of the solvents gave 26 mg of the title compound (example 2 ) as an oil. $^1$H NMR ($CDCl_3$): d 1.24 (t, 6 H), 1.37 (t, 3 H), 2.08 (s, 6 H), 2.31 (s, 3 H), 2.60 (s, 3 H), 3.58 (q, 4 H), 4.44 (q, 2 H), 6.94 (s, 2 H) ppm. The slower moving fraction, comprising the titled compound (example 3 ) was collected. Evaporation of the solvents gave 80 mg of the title compound (example 3 ) as an oil. $^1$H NMR ($CDCl_3$): d 1.32 (t, 6 H), 1.36 (t, 3 H), 1.98 (s, 6 H), 2.33 (s, 3 H), 2.47 (s, 3 H), 4.03 (q, 2 H), 3.60–4.40 (br, 4 H), 6.97 (s, 2 H) ppm.

The following compounds are prepared essentially according to procedures set forth above in Examples 1, 2, and 3.

EXAMPLE 4

N-Cyclopropylmethyl-N-propyl-2,5-dimethyl-3-(2,4,6-trimethylphenyl)2H-pyrazolo[4,3d]pyrimidin-7-amine (Compound 3).

EXAMPLE 5

N-Ethyl-N-propyl-2,5-dimethyl-3-(2,4,6-trimethylphenyl)-2H-pyrazolo[4,3-d]pyrimidin-7-amine.

EXAMPLE 6

N-Butyl-N-ethyl-2,5-dimethyl-3-(2,4,6-trimethylphenyl)-2H-pyrazolo[4,3-d]pyrimidin-7-amine.

EXAMPLE 7

N,N-Diethyl-2,5-dimethyl-3-(2,4,6-trimethylphenyl)-2H-pyrazolo[4,3-d]pyrimidin-7-amine.

EXAMPLE 8

N,N-Diallyl-2,5-dimethyl-3-(2,4,6-trimethylphenyl)-2H-pyrazolo[4,3 -d]pyrimidin-7-amine.

EXAMPLE 9

N-Ethyl-2,5-dimethyl-3-(2,4,6-trimethylphenyl)-2H-pyrazolo[4,3-d]pyrimidin-7-amine.

EXAMPLE 10

7-(1-Morpholino)-2,5-dimethyl-3-(2,4,6-trimethylphenyl)-2H-pyrazolo[4,3-d]pyrimidine.

EXAMPLE 11

N-Benzyl-N-ethyl-2,5-dimethyl-3-(2,4,6-trimethylphenyl)-2H-pyrazolo[4,3-d]pyrimidin-7-amine.

EXAMPLE 12

N,N-Di[1-(2-methoxy)ethyl]-2,5-dimethyl-3-(2,4,6-trimethylphenyl)-2H-pyrazolo[4,3-d]pyrimidin-7-amine.

The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A pharmaceutical composition comprising a compound of the formula:

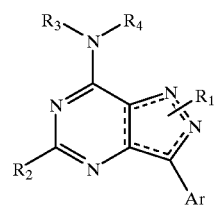

or the pharmaceutically acceptable salts thereof together with at least one pharmaceutically acceptable carrier wherein Ar is phenyl, 1- or 2-naphthyl, 2-, 3-, or 4-pyridinyl, 2- or 3-thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the pyrazole ring is substituted;

$R_1$ is lower alkyl;

$R_2$ is hydrogen, halogen, lower alkyl, lower alkoxy, or thioalkoxy having 1–6 carbon atoms;

$R_3$ and $R_4$ are the same or different and represent hydrogen, lower alkyl, alkoxy lower alkyl, hydroxy lower alkyl, or alkenyl;

phenyl, 2-, 3-, or 4-pyridinyl, 2- or 3-thienyl or 2-, 4- or 5-pyrimidinyl, each of which is optionally mono- or disubstituted with halogen, hydroxy, lower alkyl, or lower alkoxy;

phenyl-, 2-, 3-, or 4-pyridinyl-, 2- or 3-thienyl-, or 2-, 4- or 5-pyrimidinyl-lower alkyl, each of which is optionally mono- or disubstituted with lower alkyl;

cycloalkyl or cycloalkyl lower alkyl, each of which is optionally mono- or disubstituted with lower alkyl; or 2-hydroxyethyl or 3-hydroxypropyl, each of which is optionally monosubstituted with lower alkyl;

provided that not both $R_3$ and $R_4$ are hydrogen; or $R_3$ and $R_4$ taken together represent —$(CH_2)_n$—A—$(CH_2)_m$— where n is 2, or 3;

A is methylene, 1,2-phenylene, oxygen, sulfur or $NR_6$, wherein $R_6$ is lower alkyl, phenyl, 2-, 3-, or 4-pyridinyl, 2-or 3-thienyl or 2-, 4- or 5-pyrimidinyl, or phenyl, 2-, 3-or 4-pyridinyl, 2-or 3-thienyl-, or 2-, 4- or 5-pyrimidinylalkyl; and m is 1, 2 or 3.

2. A pharmaceutical composition according to claim 1, wherein the compound has the formula:

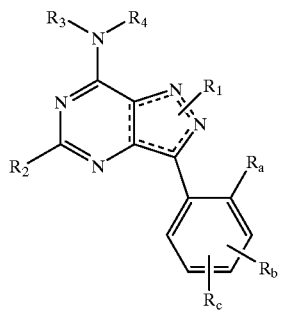

or a pharmaceutically acceptable salt thereof wherein $R_a$ represents halogen, hydroxy, lower alkyl, or lower alkoxy; $R_b$, and $R_c$ independently represent hydrogen, halogen, hydroxy, lower alkyl, or lower alkoxy;

$R_1$ is lower alkyl;

$R_2$ is hydrogen or lower alkyl; and $R_3$ and $R_4$ are the same or different and represent hydrogen, lower alkyl, lower alkenyl, cycloalkyl, cycloalkyl lower alkyl, 2-hydroxyethyl or 3-hydroxypropyl;

provided that not both $R_3$ and $R_4$ are hydrogen.

3. A pharmaceutical composition according to claim 1, wherein the compound has the formula:

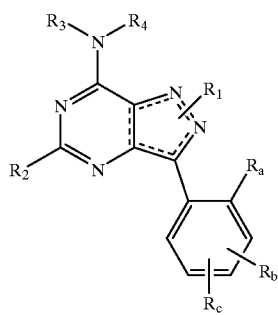

or the pharmaceutically acceptable salts thereof wherein $R_a$ represents halogen, hydroxy, lower alkyl, or lower alkoxy;

$R_b$, and $R_c$ independently represent hydrogen halogen, hydroxy, lower alkyl, or lower alkoxy;

$R_1$ is lower alkyl;

$R_2$ is hydrogen or lower alkyl; and $R_3$ and $R_4$ are the same or different and represent hydrogen, lower alkyl, cycloalkyl, cycloalkyl lower alkyl, or alkenyl;

phenyl, 2-, 3-, or 4-pyridinyl, or 2-, 4- or 5-pyrimidinyl, each of which is optionally mono- or disubstituted with halogen, hydroxy, lower alkyl, or lower alkoxy; or phenyl-, 2-, 3-, or 4-pyridinyl-, or 2-, 4- or 5-pyrimidinyl-lower alkyl, each of which is optionally mono- or disubstituted with lower alkyl;

provided that not both $R_3$ and $R_4$ are hydrogen.

4. A pharmaceutical composition according to claim 1, wherein the formula:

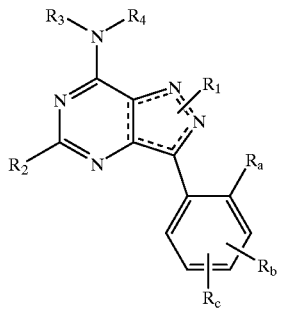

or the pharmaceutically acceptable salts thereof wherein $R_a$ represents halogen, hydroxy, lower alkyl, or lower alkoxy;

$R_b$, and $R_c$ independently represent hydrogen halogen, hydroxy, lower alkyl, or lower alkoxy;

$R_1$ is lower alkyl;

$R_2$ is hydrogen or lower alkyl; and $R_3$ and $R_4$ taken together represent —$(CH_2)_n$—A—$(CH_2)_m$— where n is 2, or 3;

A is methylene, 1,2-phenylene, oxygen, sulfur or $NR_6$, wherein $R_6$ is lower alkyl, phenyl, 2-, 3-, or 4-pyridinyl, 2-or 3-thienyl or 2-, 4- or 5-pyrimidinyl, or phenyl, 2-, 3-or 4-pyridinyl-, 2-or 3-thienyl-, or 2-, 4- or 5-pyrimidinylalkyl; and m is 1, 2 or 3.

5. A pharmaceutical composition according to claim 1, wherein the compound has the formula:

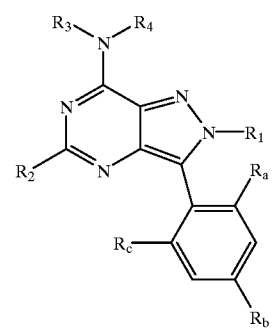

or the pharmaceutically acceptable salts thereof wherein $R_a$, $R_b$, and $R_c$ independently represent hydrogen, halogen, hydroxy, lower alkyl, or lower alkoxy, with the proviso that not both $R_a$ and $R_c$ are hydrogen;

$R_1$ is lower alkyl;

$R_2$ is hydrogen or lower alkyl; and $R_3$ and $R_4$ are the same or different and represent hydrogen, lower alkyl, cycloalkyl, cycloalkyl lower alkyl, alkenyl, 2-hydroxyethyl or 3-hydroxypropyl, provided that not both $R_3$ and $R_4$ are hydrogen.

6. A pharmaceutical composition according to claim 5, wherein $R_a$, $R_b$, and $R_c$ are methyl.

7. A pharmaceutical composition according to claim 6, wherein $R_1$ and $R_2$ independently represent lower alkyl.

8. A pharmaceutical composition according to claim 1, wherein the compound has the formula:

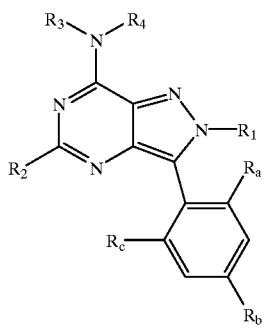

or the pharmaceutically acceptable salts thereof wherein
$R_a$, $R_b$, and $R_c$ independently represent hydrogen, halogen, hydroxy, lower alkyl, or lower alkoxy, with the proviso that not both $R_a$ and $R_c$ are hydrogen;
$R_1$ is lower alkyl;
$R_2$ is hydrogen or lower alkyl; and
$R_3$ and $R_4$ are the same or different and represent hydrogen, lower alkyl, cycloalkyl, cycloalkyl lower alkyl, alkenyl, 2-hydroxyethyl or 3-hydroxypropyl, provided that not both $R_3$ and $R_4$ are hydrogen.

9. A pharmaceutical composition according to claim 8, wherein $R_a$, $R_b$, and $R_c$ are methyl.

10. A pharmaceutical composition according to claim 9, wherein $R_1$ and $R_2$ independently represent lower alkyl.

11. A method of treating stress disorders comprising administering to a patient in need of such treatment a compound of the formula:

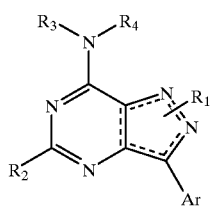

or the pharmaceutically acceptable salts thereof together with wherein Ar is phenyl, 1- or 2-naphthyl, 2-, 3-, or 4-pyridinyl,
2- or 3-thienyl, 4- or 5-pyrimidinyl, each of which is mono-, di-, or trisubstituted with halogen, hydroxy, lower alkyl, or lower alkoxy, provided that at least one of the positions on Ar ortho to the point of attachment to the pyrazole ring is substituted;
$R_1$ is lower alkyl;
$R_2$ is hydrogen, halogen, lower alkyl, lower alkoxy, or thioalkoxy having 1–6 carbon atoms;
$R_3$ and $R_4$ are the same or different and represent hydrogen, lower alkyl, alkoxy lower alkyl, hydroxy lower alkyl, or alkenyl;
phenyl, 2-, 3-, or 4-pyridinyl, 2- or 3-thienyl or 2-, 4- or 5-pyrimidinyl, each of which is optionally mono- or disubstituted with halogen, hydroxy, lower alkyl, or lower alkoxy;
phenyl-, 2-, 3-, or 4-pyridinyl-, 2- or 3-thienyl-, or 2-, 4- or 5-pyrimidinyl-lower alkyl, each of which is optionally mono- or disubstituted with lower alkyl;
cycloalkyl or cycloalkyl lower alkyl, each of which is optionally mono- or disubstituted with lower alkyl; or
2-hydroxyethyl or 3-hydroxypropyl, each of which is optionally monosubstituted with lower alkyl;
provided that not both $R_3$ and $R_4$ are hydrogen; or
$R_3$ and $R_4$ taken together represent —$(CH_2)_n$—A—$(CH_2)_m$— where is 2, or 3;
A is methylene, 1,2-phenylene, oxygen, sulfur or $NR_6$, wherein $R_6$ is lower alkyl, phenyl, 2-, 3-, or 4-pyridinyl, 2-or 3-thienyl or 2-, 4- or 5-pyrimidinyl, or phenyl, 2-, 3-or 4-pyridinyl-, 2-or 3-thienyl-, or 2-, 4- or 5-pyrimidinylalkyl; and
m is 1, 2 or 3
to a patient in need thereof.

12. A method according to claim 11, where the stress disorder is post traumatic stress disorder.

13. A method according to claim 12, where the stress disorder is depression.

14. A method according to claim 12, where the stress disorder is anxiety.

* * * * *